United States Patent
Hai (10) Patent No.: US 10,120,217 B2
(45) Date of Patent: Nov. 6, 2018

(54) METHOD FOR MEASURING THE LIQUID CRYSTAL EFFICIENCY OF THE LIQUID CRYSTAL LAYER TO THE INCIDENT LIGHT

(71) Applicant: Shenzhen China Star Optoelectronics Technology Co., Ltd., Shenzhen, Guangdong (CN)

(72) Inventor: Bo Hai, Guangdong (CN)

(73) Assignee: Shenzhen China Star Optoelectronics Technology Co., Ltd, Shenzhen, Guangdong (CN)

( * ) Notice: Subject to any disclaimer, the term of this patent is extended or adjusted under 35 U.S.C. 154(b) by 183 days.

(21) Appl. No.: 15/102,734

(22) PCT Filed: May 19, 2016

(86) PCT No.: PCT/CN2016/082597
§ 371 (c)(1),
(2) Date: Jun. 8, 2016

(87) PCT Pub. No.: WO2017/181467
PCT Pub. Date: Oct. 26, 2017

(65) Prior Publication Data
US 2018/0081210 A1    Mar. 22, 2018

(30) Foreign Application Priority Data
Apr. 18, 2016    (CN) .......................... 2016 1 0242290

(51) Int. Cl.
G02F 1/13    (2006.01)
G01N 21/59    (2006.01)
(Continued)

(52) U.S. Cl.
CPC .......... *G02F 1/1309* (2013.01); *G01M 11/00* (2013.01); *G01M 11/0285* (2013.01);
(Continued)

(58) Field of Classification Search
CPC ...... G01N 21/21; G01N 21/25; G01N 21/255; G01N 21/27; G01N 21/274; G01N 21/29;
(Continued)

(56) References Cited

U.S. PATENT DOCUMENTS 7,619,726 B2 * 11/2009 Wang ..................... G01N 21/27
349/106
9,244,303 B2   1/2016 Xuan et al.
(Continued)

FOREIGN PATENT DOCUMENTS

| CN | 101178488 A | 5/2008 |
|----|-------------|--------|
| CN | 101685207 A | 3/2010 |

(Continued)

*Primary Examiner* — Gordon J Stock, Jr.
(74) *Attorney, Agent, or Firm* — Andrew C. Cheng (57) ABSTRACT

The present disclosure providing a method for measuring the liquid crystal efficiency of the liquid crystal layer to the incident light, the method includes: keeping the lower polarizing plate unchanged to make the upper polarizing plate and the lower polarizing of the liquid crystal layer in a first state; in the first state, controlling the brightness of the screen of the liquid crystal panel to be 0 gray and to be 255 to measure the brightness Lvx and Lvy of the target position of the liquid crystal panel, respectively; according to the brightness Lvx and the brightness Lvy, determining the liquid crystal efficiency of the liquid crystal layer to the incident light. By the above method, the present disclosure could be performed without disassembling the module, number of the measurements is few and simple, and the efficiency and the accuracy are high.

13 Claims, 4 Drawing Sheets

(51) Int. Cl.
  *G01M 11/02* (2006.01)
  *G01N 21/25* (2006.01)
  *G09G 3/00* (2006.01)
  *G01M 11/00* (2006.01)
  *G01N 21/21* (2006.01)

(52) U.S. Cl.
  CPC ............. *G01N 21/21* (2013.01); *G01N 21/25* (2013.01); *G01N 21/59* (2013.01); *G09G 3/006* (2013.01)

(58) Field of Classification Search
  CPC .... G01N 21/59; G01N 21/5911; G01N 21/17; G01N 21/1717; G01N 21/5907; G01N 21/62; G01N 21/66; G01N 21/70; G01N 21/88; G01N 21/8803; G01N 21/95; G01N 2021/1721; G01N 2021/1734; G01N 2021/1738; G01N 2021/1761; G01N 2021/1765; G01N 2021/1768; G01N 2021/177; G01N 2021/1772; G01N 2021/1774; G01N 2021/1776; G01N 2021/214; G01N 2021/218; G01N 2021/5915; G01N 2021/5938; G01N 2021/5957; G01N 2021/8477; G01N 2021/9513; G02F 1/1309; G01M 11/00; G01M 11/0285; G01M 11/08; G09G 3/006

See application file for complete search history.

(56) References Cited

U.S. PATENT DOCUMENTS

| | | | | |
|---|---|---|---|---|
| 9,477,102 B2* | 10/2016 | Wang | ................... | G02B 6/0043 |
| 9,530,337 B2* | 12/2016 | Hu | ......... | G09G 3/006 |
| 9,709,495 B2* | 7/2017 | Kim | ..................... | G01N 21/59 |
| 9,818,320 B2* | 11/2017 | Ma | ......... | G09G 3/006 |
| 2006/0001809 A1 | 1/2006 | Lee et al. | | |
| 2014/0022501 A1 | 1/2014 | Wang | | |
| 2016/0322006 A1* | 11/2016 | Chen | ................... | G09G 3/3426 |
| 2017/0047047 A1* | 2/2017 | Zhao | ........................ | G09G 5/10 |
| 2017/0263172 A1* | 9/2017 | Chen | ................... | G09G 3/2003 |

FOREIGN PATENT DOCUMENTS

| | | | | |
|---|---|---|---|---|
| CN | 102213848 A | | 10/2011 | |
| CN | 105049842 A | * | 11/2015 | ............. G01N 21/59 |
| CN | 105334649 A | | 2/2016 | |

* cited by examiner

METHOD FOR MEASURING THE LIQUID CRYSTAL EFFICIENCY OF THE LIQUID CRYSTAL LAYER TO THE INCIDENT LIGHT

FIELD OF THE DISCLOSURE

The present disclosure relates to a liquid crystal technology field, and more particularly to a method for measuring the liquid crystal efficiency of the liquid crystal layer to the incident light.

BACKGROUND OF THE DISCLOSURE

The most commonly used display mode of the liquid crystal panel includes twisted nematic (TN) mode, vertical alignment (VA) mode and in plain switching (IPS) mode.

Using VA mode as an example: VA display is a normally black mode of vertically aligned and its polarization axis of the upper polarizing plate and the lower polarizing plate is vertical polarizer attachment. The principle of the VA liquid crystal display is based on the characteristic of the light transmittance changed with the size of the applied voltage. After the light through the polarizing plate of the lower substrate (i.e. TFT substrate), the light become linearly polarized light, the direction of the polarization is the direction of the polarization axis of the lower polarizing plate. When no voltage is applied, the light through the liquid crystal will not change the direction of the polarization, and the light will be received through the polarizing plate of the upper substrate (i.e. CF substrate), so that will be a dark state. After applying the voltage, the liquid crystal is deflected alone the alignment direction in the electric field. When the light is through the liquid crystal layer, the linearly polarized light is divided into two beams due to the refraction of the liquid crystal. Also, because of the two different beams of the propagation velocity, after synthesize the two beams, is bound to change the polarization direction of the polarized light. When the incident light reaches the polarizing plate of the upper substrate, the light parallel to the polarization axis direction of the lower polarizing plate can pass through, thus being a bright state. In the whole process of display, the liquid crystal has played the role of the light valve controlled by the voltage. This shows that the liquid crystal deflection capability of the polarization direction of the linearly polarized light is very important, it directly affects the result of the penetration.

The liquid crystal efficiency of the liquid crystal layer to the incident light is defined as: the polarized light generated by through the lower polarizing plate and parallel the direction of the polarization axis of the lower polarizing plate, in the maximum gray, exclude the absorb factors of the liquid crystal material, and after through the liquid crystal layer, what percentage of the direction of the polarization of the incident light can be deflected 90 degrees by the liquid crystal layer to penetrate out the light. In the prior art, the conventional method for measuring the liquid crystal efficiency is: measuring the transmittance of the liquid crystal panel many times, and excluding other factors of affecting transmittance by calculating, then calculated the liquid efficiency. However, the measurement of this method is more often, the variation in the measurement process is more, and made the approximations, the efficiency and accuracy are low.

SUMMARY OF THE DISCLOSURE

The technical problem of the present disclosure solved is to provide a method for measuring the liquid crystal efficiency of the liquid crystal layer to the incident light without disassembling the module, and number of the measurements is few and simple, and further the efficiency and the accuracy are high.

To solve the above technical problems, one aspect of the present disclosure used is: providing a method for measuring the liquid crystal efficiency of the liquid crystal layer to the incident light, wherein the method includes: keeping the lower polarizing plate of the liquid crystal layer unchanged to make the upper polarizing plate and the lower polarizing plate of the liquid crystal are in a first state, in which the polarization axis of the upper polarizing plate is parallel to the polarization axis of the lower polarizing plate;

in the first state, controlling the brightness of the screen of the liquid crystal panel to be 0 gray and measuring the brightness Lvx of the target position of the liquid crystal panel;

in the first state, controlling the brightness of the screen of the liquid crystal panel to be 255 gray and measuring the brightness Lvy of the target position of the liquid crystal panel;

according to the brightness Lvx and the brightness Lvy, determining the liquid crystal efficiency of the liquid crystal layer to the incident light;

wherein, the liquid crystal efficiency A of the liquid crystal layer to the incident light is:

$$A = \left\{1 - \frac{Lvy}{Lvx}\right\}\%$$

or, before the step of keeping the lower polarizing plate of the liquid crystal layer unchanged to make the upper polarizing plate and the lower polarizing plate of the liquid crystal in the first state, the method further includes:

making the upper polarizer plate and the lower polarizer plate of the liquid crystal layer to be in a second state, in which the polarization axis of the upper polarizing plate is perpendicular to the polarization axis of the lower polarizing plate;

in the second state, controlling the brightness of the screen of the liquid crystal panel to be 0 gray and measuring the brightness Lvz of the target position of the liquid crystal panel;

the step of determining the liquid crystal efficiency A of the liquid crystal layer to the incident light according to the brightness Lvx and the brightness Lvy includes:

determining the liquid crystal efficiency of the liquid crystal layer B to the incident light according to the brightness Lvx, the brightness Lvy and the brightness Lvz.

Wherein, the liquid crystal efficiency B of the liquid crystal layer to the incident light is:

$$B = \left\{1 - \frac{Lvy}{Lvx + Lvz}\right\}\%$$

wherein, the step of keeping the lower polarizing plate of the liquid crystal layer unchanged to make the upper polarizing plate and the lower polarizing plate of the liquid crystal in the first state, includes: in the second state, removing the original upper polarizing plate, using the new polarizing plate of the same model of the original upper polarizing plate as the upper polarizing plate, and attaching the new polarizing plate by deflecting 90 degrees from a polarizer attach direction along which the original upper polarizing plate being attached so as to make the upper polarizing plate and the lower polarizing plate of the liquid crystal layer to be in the first state.

In order to solve the above problems, another aspect of the present disclosure used is: providing a method for measuring the liquid crystal efficiency of the liquid crystal layer to the incident light, wherein the method includes: keeping the lower polarizing plate of the liquid crystal layer unchanged to make the upper polarizing plate and the lower polarizing plate of the liquid crystal to be in a first state, in which the polarization axis of the upper polarizing plate is parallel to the polarization axis of the lower polarizing plate; in the first state, controlling the brightness of the screen of the liquid crystal panel to be 0 gray and measuring the brightness $Lvx$ of the target position of the liquid crystal panel; in the first state, controlling the brightness of the screen of the liquid crystal panel to be 255 gray and measuring the brightness $Lvy$ of the target position of the liquid crystal panel; according to the brightness $Lvx$ and the brightness $Lvy$, determining the liquid crystal efficiency A of the liquid crystal layer to the incident light.

Wherein, the liquid crystal efficiency A of the liquid crystal layer to the incident light is:

$$A = \left\{1 - \frac{Lvy}{Lvx}\right\}\%$$

Wherein, before the step of keeping the lower polarizing plate of the liquid crystal layer unchanged to make the upper polarizing plate and the lower polarizing plate of the liquid crystal to be in the first state, includes: making the upper polarizer plate and the lower polarizer plate of the liquid crystal layer in a second state, in which the polarization axis of the upper polarizing plate is perpendicular to the polarization axis of the lower polarizing plate; in the second state, controlling the brightness of the screen of the liquid crystal panel to be 0 gray and measuring the brightness $Lvz$ of the target position of the liquid crystal panel; the step of determining the liquid crystal efficiency A of the liquid crystal layer to the incident light according to the brightness $Lvx$ and the brightness $Lvy$ includes: determining the liquid crystal efficiency B of the liquid crystal layer to the incident light according to the brightness $Lvx$, the brightness $Lvy$ and the brightness $Lvz$.

Wherein, the liquid crystal efficiency B of the liquid crystal layer to the incident light is:

$$B = \left\{1 - \frac{Lvy}{Lvx + Lvz}\right\}\%$$

Wherein, the step of keeping the lower polarizing plate of the liquid crystal layer unchanged to make the upper polarizing plate and the lower polarizing plate of the liquid crystal to be in the first state, includes: in the second state, removing the original upper polarizing plate, using the new polarizing plate of the same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

In order to solve the above problems, the other aspect of the present disclosure used is: providing a method for measuring the liquid crystal efficiency of the liquid crystal layer to the incident light in the predetermined gray, wherein, the method includes: keeping the lower polarizing plate of the liquid crystal layer unchanged to make the upper polarizing plate and the lower polarizing plate of the liquid crystal to be in a first state, in which the polarization axis of the upper polarizing plate is parallel to the polarization axis of the lower polarizing plate; in the first state, controlling the brightness of the screen of the liquid crystal panel to be 0 gray and measuring the brightness $Lvx$ of the target position of the liquid crystal panel; in the first state, controlling the brightness of the screen of the predetermined color of the liquid crystal panel to be the predetermined gray and measuring the brightness $Lvy'$ of the target position of the liquid crystal panel; according to the brightness $Lvx$ and the brightness $Lvy'$, determining the liquid crystal efficiency A' of the liquid crystal layer to the incident light of the predetermined color in the predetermined gray.

Wherein, the liquid crystal efficiency A' of the liquid crystal layer to the incident light of the predetermined color in the predetermined gray is:

$$A' = \left\{1 - \frac{Lvy'}{Lvx}\right\}\%$$

Wherein, before the step of keeping the lower polarizing plate of the liquid crystal layer unchanged to make the upper polarizing plate and the lower polarizing plate of the liquid crystal to be in the first state, includes: making the upper polarizer plate and the lower polarizer plate of the liquid crystal layer to be in a second state, in which the polarization axis of the upper polarizing plate is perpendicular to the polarization axis of the lower polarizing plate; in the second state, controlling the brightness of the screen of the liquid crystal panel to be 0 gray and measuring the brightness $Lvz'$ of the target position of the liquid crystal panel; the step of determining the liquid crystal efficiency A' of the liquid crystal layer to the incident light according to the brightness $Lvx$ and the brightness $Lvy'$ includes: determining the liquid crystal efficiency B' of the liquid crystal layer to the incident light of the predetermined color in the predetermined gray according to the brightness $Lvx$, the brightness $Lvy'$ and the brightness $Lvz'$.

Wherein, the liquid crystal efficiency B' of the liquid crystal layer to the incident light of the predetermined color in the predetermined gray is:

$$B' = \left\{1 - \frac{Lvy'}{Lvx + Lvz'}\right\}\%$$

Wherein, the step of keeping the lower polarizing plate of the liquid crystal layer unchanged to make the upper polarizing plate and the lower polarizing plate of the liquid crystal to be in the first state, includes: in the second state, removing the original upper polarizing plate, using the new polarizing plate of the same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

The beneficial effects of the present disclosure are: the situation is different from the prior art, the present disclosure keeps the lower polarizing plate unchanged to make the upper polarizing plate and the lower polarizing of the liquid crystal layer to be in a first state, in which the polarization axis of the upper polarizing plate is parallel to the polarization axis of the lower polarizing plate; in the first state, controlling the brightness of the screen of the liquid crystal panel to be 0 gray and measuring the brightness Lvx of the target position of the liquid crystal panel; in the first state, controlling the brightness of the screen of the liquid crystal panel to be 255 gray and measuring the brightness Lvy of the target position of the liquid crystal panel; according to the brightness Lvx and the brightness Lvy, determining the liquid crystal efficiency of the liquid crystal layer to the incident light. By the above method, the measurement of the transmittance in the prior art can be avoided, without disassembling the back light module, the effect of the transmittance fluctuation caused by disassembly can be avoid so that measurement is more accurate and simpler; at the same time, without using the control group, the measured data is measured in the same back light brightness state, and the measured data is accurate.

DETAILED DESCRIPTION OF PREFERRED EMBODIMENTS

Prior to the detailed description of the present disclosure, the technologies relating to the present disclosure are explained first.

Figure 1:
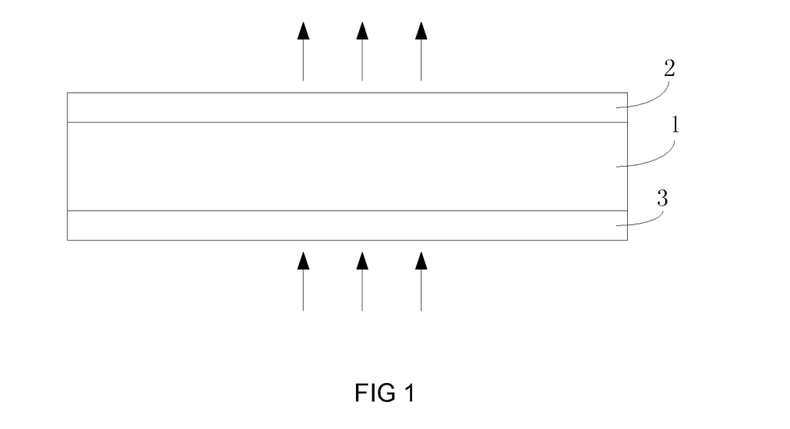
FIG. 1 is a schematic diagram of measuring the liquid crystal efficiency in the prior art.
Figure 2:
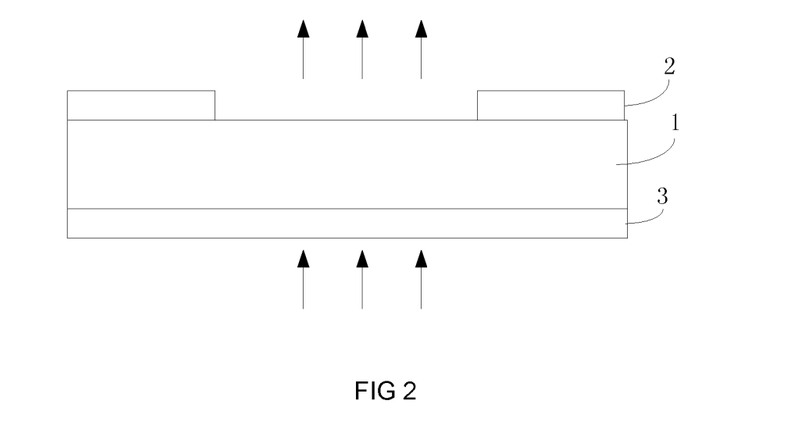
FIG. 2 is another schematic diagram of measuring the liquid crystal efficiency in the prior art.
Figure 3:
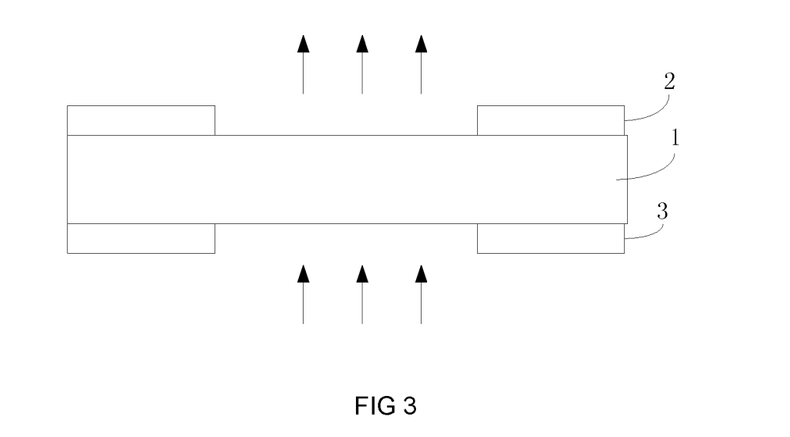
FIG. 3 is the other schematic diagram of measuring the liquid crystal efficiency in the prior art.

One of the method for measuring the liquid crystal efficiency of the liquid crystal layer to the incident light in the prior art is as follows:

Refer to FIG. 1 to FIG. 3, the middle is the liquid crystal layer 1, the top of the liquid crystal layer 1 is the upper polarizing plate 2, the bottom of the liquid crystal layer 1 is the lower polarizing plate 3.

As shown in FIG. 1, in the first step, the normal transmittance of the liquid crystal panel is measured, L is the brightness of the back light source, and $L_1$ is the brightness after through the liquid crystal cell. Accordingly, the following equation can be drawn:

$$T = L_1/L = \eta_{lower\ to\ natural} * AR * \eta_{CF} * \eta_{LC} * \eta_{upper\ to\ polarized} \qquad (1)$$

T is the total transmittance after through the liquid crystal cell in the FIG. 1, the $\eta_{lower\ to\ natural}$ is the transmittance of the lower polarizing plate to the natural light, the AR is the aperture ratio, $\eta_{CF}$ is the transmittance of the color filter (CF), $\eta_{LC}$ is the liquid crystal efficiency, i.e. the transmittance of the liquid crystal layer, $\eta_{upper\ to\ polarized}$ is the transmittance of the upper polarizing plate to the polarized light.

As shown in FIG. 2, in the second step, the polarizing plate of the upper substrate (i.e. the CF substrate) is stripped, and the transmittance of the liquid crystal panel is measured, wherein $L_2$ is the brightness after stripping the upper polarizing plate 2 and through the liquid crystal cell. Accordingly, the following equation can be drawn:

$$T' = L_2/L = \eta_{lower\ to\ natural} * AR * \eta_{CF} \qquad (2)$$

Wherein, the T' is the total transmittance after through the liquid crystal cell in the FIG. 2.

As shown in FIG. 3, in the third step, the upper polarizing plate and the lower polarizing plate are stripped at same time and the transmittance of the liquid crystal panel is measured, wherein $L_3$ is the brightness after stripping the upper polarizing plate 2 and the lower polarizing plate 3 and through the liquid crystal cell. Accordingly, the following equation can be drawn:

$$T'' = L_3/L = AR * \eta_{CF} \qquad (3)$$

Wherein, the T'' is the total transmittance after through the liquid crystal cell.

According to the relationship (1)(2)(3), the following equations can be drawn:

$$T/T' = \eta_{LC} * \eta_{upper\ to\ polarized} \qquad (4)$$

$$T'/T'' = \eta_{lower\ to\ natural} \qquad (5)$$

Suppose the following relationship:

$$\eta_{upper\ to\ polarized} = 2 * \eta_{upper\ to\ natural} \qquad (6)$$

$$\eta_{lower\ to\ polarized} = 2 * \eta_{lower\ to\ natural} \qquad (7)$$

According to the relationship (4)(5)(6)(7), the liquid crystal efficiency can be drawn:

$$\eta_{LC} = T * T''/2T'^2 \qquad (8)$$

By the above calculations and excluding other factors of the transmittance, the efficiency of the liquid crystal is calculated.

In the above measurements, measuring the transmittance three times is needed. The number of the measurements is more, because the measurement of the transmittance needs measuring the brightness of the back light and the module respectively, not simultaneous measurement, every time of the disassembly and the human factors will affect the measurement results of the transmittance, the transmittance in the measurement process is susceptible to mutation; the transmittance to the polarizing plate made approximations, the efficiency and the accuracy of the measurement are lowered; the upper polarizing plate and the lower polarizing plate are destroyed, and increase the difficulty and the cost of the re-use of the polarizer attachment.

The present disclosure provides a new measurement principle, and designs a new method for measuring the liquid crystal efficiency, thereby simplifies the measurement and increases the measuring efficiency; simultaneously, the measurement data of the present disclosure is measured in the same time period without using control group and disassembling back light, so that the accuracy is improved and the difficulty and the cost of the re-use of the polarizer attachment are reduced.

The accompanying drawings and the following embodiments of the present disclosure will be described in detail.

The principle of the measurement of the present disclosure is introduced first.

The light emitted by the back light source generates the linearly polarized light parallel to the direction of the polarization axis of the lower polarizing plate after through the lower polarizing plate (TFT substrate). In the maximum gray, excluding the absorb factors of the liquid crystal material, because the liquid crystal azimuth or the design of the liquid crystal optical path difference makes the liquid crystal to be not completely ½ slide, not all the polarization direction of the incident light deflect 90 degrees after through the liquid crystal layer and are parallel with the polarization axis of the polarizing plate of the upper substrate (CF substrate) to throughout therefrom. The liquid crystal efficiency for enhancing transmittance is very important, so it is necessary to evaluate the liquid crystal efficiency of the liquid crystal panel.

Figure 4:
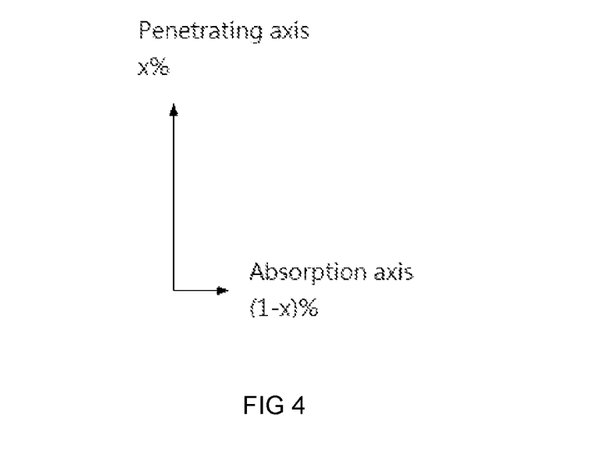
FIG. 4 is a schematic diagram of measuring the liquid crystal efficiency of the liquid crystal layer to the incident light of the present disclosure.

The normal VA mode and IPS mode is the normal black mode, i.e. the direction of the polarization axis of the upper polarizing plate is vertical to the direction of the polarization axis of the lower polarizing plate. Suppose the liquid crystal efficiency in 255 gray is x % in a bright state, according to the wave optics theory, all the outgoing light can be decomposed to the deflected linearly polarized light paralleling with the direction of the polarization axis of the polarizing plate of the upper substrate and the deflected linearly polarized light being vertical to the direction of the polarization axis of the polarizing plate of the upper substrate (i.e. the transmission direction and the absorption direction perpendicular to each other). As shown in FIG. 4, when there is x % of the incident light along the transmission direction (penetrating axis), the remaining (1−x) % incident light is along the absorption direction (absorption axis), i.e. while being in bright state, the incident ratio of the penetrating axis and the absorption axis in the bright state is shown in FIG. 4.

Figure 5:
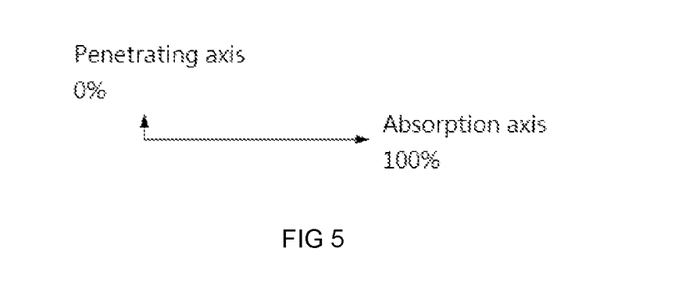
FIG. 5 is another schematic diagram of measuring the liquid crystal efficiency of the liquid crystal layer to the incident light of the present disclosure.

While being in the dark state with 0 gray, the incident ratio of the penetrating axis and the absorption axis in the dark state is as that shown in FIG. 5 because the IPS contrast is about 1000, the VA mode contrast is over 4000, the brightness of dark state is very low, and the brightness of the bright state is much larger than the dark state, i.e., it can be deemed that there is no light passing along the direction of the penetrating axis of the upper polarizing plate while the incident light is absorbed by travelling along the direction of the absorption axis of the upper polarizing plate and cannot through therefrom.

The upper polarizing plate is removed and then the new polarizing plate with same model is used to re-post the upper polarizing plate along a direction which is deflected 90 degrees from the removed upper polarizing plate, i.e. the direction of the polarization axis of the upper polarizing plate is parallel to the direction of the polarization axis of the lower polarizing plate. This is the normally white mode, i.e. when no voltage is applied, the liquid crystal does not change the polarization direction of the linearly polarized light and, because the polarization axis of the upper polarizing plate is parallel to the polarization axis of the lower polarizing plate, the linearly polarized light generated by passing incident light through the lower polarizing plate is through the transmission direction of the upper polarizing plate directly to display a white screen. The liquid crystal efficiency is 100% at this time and the brightness Lvx of the panel is measured. After that, the gray value is switched to the maximum gray (i.e. 255 gray), and the brightness Lvy of the panel, which is the brightness through the transmission direction of the upper polarizing plate after being deflected by the liquid crystal, i.e., the brightness through the absorption direction of the upper polarizing plate of the original normal black mode module, is measured. (Lvy/Lvx) % is the ratio of the incident light through the absorption direction of the polarizing plate of the upper substrate, and therefore the ratio of the incident light through the transmission direction of the polarizing plate of the upper substrate, i.e., the liquid crystal efficiency, is {1−(Lvy/Lvx)} %. When re-posting the upper polarizing plate, the upper polarizing plate deflected 90 degrees. When the penetrating axis of the upper polarizing plate is parallel to the penetrating axis of the lower polarizing plate, the brightness of the bright state of the 255 gray and the dark state of the 0 gray are measured, respectively, and are the (1−x) % incident light of the absorption axis in the bright state and the 100% incident light of the absorption axis in the dark state shown in FIG. 4, respectively.

Figure 6:
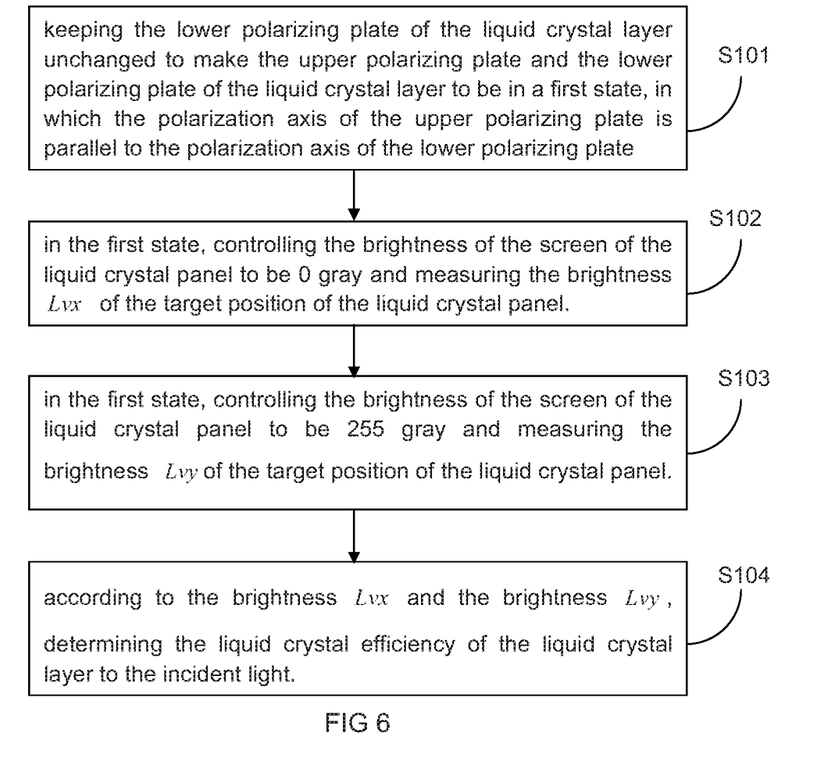
FIG. 6 is a flow chart of an embodiment of the method for measuring the liquid crystal efficiency of the liquid crystal layer to the incident light of the present disclosure.

Refer to FIG. 6. FIG. 6 is a flow chart of an embodiment of the method for measuring the liquid crystal efficiency of the liquid crystal layer to the incident light of the present disclosure. The method includes:

Step S101: keeping the lower polarizing plate of the liquid crystal layer unchanged to make the upper polarizing plate and the lower polarizing plate of the liquid crystal layer to be in a first state, in which the polarization axis of the upper polarizing plate is parallel to the polarization axis of the lower polarizing plate.

Usually, the dark state brightness of the normal black mode is very low. E.g. the brightness is 400 and the contrast is 4000, then the dark state brightness is 0.1. Therefore, when no voltage is applied in the normal black mode, the effect of the liquid crystal to deflect the linearly polarized light can be ignored.

Figure 7:
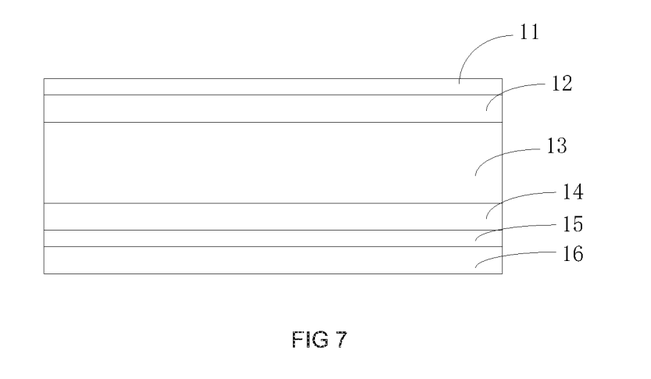
FIG. 7 is a schematic structure view of the liquid crystal panel in the prior art.

Refer to FIG. 7, which is a schematic structure view of the liquid crystal panel, the liquid crystal panel from top to bottom includes an upper polarizing plate 11, an upper substrate 12, a liquid crystal layer 13, a lower substrate 14, a lower polarizing plate 15 and a back light module 16.

The first state is the parallel state in which the polarization axis of the upper polarizing plate is parallel to the polarization axis of the lower polarizing plate. Keeping the lower polarizing plate of the liquid crystal layer unchanged to make the upper polarizing plate and the lower polarizing plate of the liquid crystal layer in the first state means that it is not necessary to dismantle the lower polarizing plate 15 and the back light module 16. When needed, only the upper polarizer 11 is changed so that the polarization axis of the upper polarizing plate is changed by 90 degrees in order to make the upper polarizing plate and the lower polarizing plate of the liquid crystal layer to be in the first state.

For the VA display mode, the IPS display mode and the TN display mode, the upper polarizing plate and the lower polarizing plate are attached in a way making the polarization axis of the upper polarizing plate to be vertical to the polarization axis of the low polarizing plate, which is referred to as the second state.

In this case, the step S101 can be: in the second state, removing the original upper polarizing plate, using the new polarizing plate of the same model of the original upper polarizing plate as the upper polarizing plate and attaching the new polarizing plate by deflecting 90 degrees from a polarizer attach direction along which the original upper polarizing plate being attached, so as to make the upper polarizing plate and the lower polarizing plate of the liquid crystal layer to be in the first state.

It should be noted that, first, the more the re-posted upper polarizing plate type is close to the polarizing plate of the original panel, the less the polarizing plate affects the result; the polarizing plate with the same type and the same batch of the polarizing plate of the original panel is preferred. Second, when re-posting, the accuracy is required; if the polarizing plate is going to be attached manually a signal can be provided to the liquid crystal back light module when attaching so that the attachment can be performed along the direction in which the pixel arranged. Third, if a machine is selected to complete the attachment, because of the size problem, the lower polarizing with the same type and the same batch can be chose and attached to the upper substrate; or the upper polarizing plate is cut before completing attachment.

By the above method, the measurement of the transmittance in the prior art can be avoided, and it is not necessary to disassemble the back light module so that the effect of the transmittance fluctuation caused by disassembly can be avoid and the measurement can be more accurate and simpler; at the same time, without using the control group, the measured data is measured in the same back light brightness state so that the measured data is accurate.

Step S102: in the first state, controlling the brightness of the screen of the liquid crystal panel to be 0 gray and measuring the brightness Lvx of the target position of the liquid crystal panel.

Step S103: in the first state, controlling the brightness of the screen of the liquid crystal panel to be 255 gray and measuring the brightness Lvy of the target position of the liquid crystal panel.

Step S104: according to the brightness Lvx and the brightness Lvy, determining the liquid crystal efficiency of the liquid crystal layer to the incident light.

The brightness Lvx is a brightness measured in the normally white mode, i.e. when no voltage is applied, the liquid crystal does not change the polarization direction of the linearly polarized light, and, because the polarization axis of the upper polarizing plate is parallel to the polarization axis of the lower polarizing plate, the linearly polarized light generated by through the lower polarizing plate is through along the transmission direction of the upper polarizing plate directly so that a white screen is displayed and the liquid crystal efficiency is 100%.

The brightness Lvy is a brightness measured while switching to the maximum gray (i.e. 255 gray), this brightness is the brightness through along the transmission direction of the upper direction after being deflected by the liquid crystal, that is, the brightness passing through along the absorption direction of the upper polarizing plate in the normally black mode of the original module.

If there are some other correction factors, the correction factors, the brightness Lvx and the brightness Lvy can be combined either by experience or a given formula, etc., and the liquid crystal efficiency of the liquid crystal layer to the incident light can be determined accordingly.

In an embodiment, if the affection of the correction factors or other factors are ignored, the liquid crystal efficiency A of the liquid crystal layer to the incident light is:

$$A = \left\{1 - \frac{Lvy}{Lvx}\right\}\%$$

Figure 8:
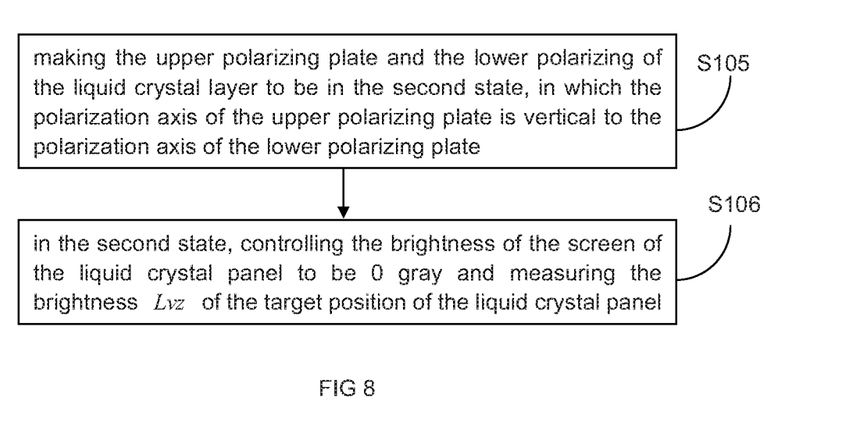
FIG. 8 is a flow chart of another embodiment of the method for measuring the liquid crystal efficiency of the liquid crystal layer to the incident light of the present disclosure.

Once the contrast of the liquid crystal panel is very low and the brightness of the dark state is very high, it means that, when no voltage is applied thereto in the normally dark mode, the liquid crystal deflects the linearly polarized light, the liquid crystal efficiency is not 100%, and the brightness Lvz of the dark state in the normally black mode is needed to be measured first and then measuring with the above method. Refer to FIG. 8, step S105 and step S106 is further included and performed before the step S101.

Step S105: making the upper polarizing plate and the lower polarizing of the liquid crystal layer to be in the second state, in which the polarization axis of the upper polarizing plate is vertical to the polarization axis of the lower polarizing plate.

Step S106: in the second state, controlling the brightness of the screen of the liquid crystal panel to be 0 gray and measuring the brightness Lvz of the target position of the liquid crystal panel;

At this time, the step S104 specifically includes: according to the brightness Lvx, the brightness Lvy and the brightness Lvz, determining the liquid crystal efficiency of the liquid crystal layer to the incident light.

If there are some other correction factors, the correction factor, the brightness Lvx, the brightness Lvy and the brightness Lvz are combined by experience or a given formula, etc., and the liquid crystal efficiency of the liquid crystal layer to the incident light can be determined.

Wherein, if the affection of the correction factors or other factors are ignored, the liquid crystal efficiency B of the liquid crystal layer to the incident light is:

$$B = \left\{1 - \frac{Lvy}{Lvx + Lvz}\right\}\%$$

Wherein, the step S101 can be: in the second state, removing the original upper polarizing plate, using the new polarizing plate of the same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

The following specific experimental data are used to illustrate the beneficial effects of the present disclosure. The comparative method is the prior art method shown in FIG. 1 to FIG. 3. Table 1 shows the test data of the liquid crystal efficiency measured by the comparative method, table 2 shows the test data of the liquid crystal efficiency measured by the method of the disclosure without considering the brightness of the dark state, and table 3 shows the test data of the liquid crystal efficiency measured by the method of the disclosure while considering the brightness of the dark state.

TABLE 1

Comparative Method

| | First time | Second time | Third time | Fourth time |
|---|---|---|---|---|
| Original module | 308.6 | 312.7 | 280.9 | 292.1 |
| BLU | 4566.3 | 4601.6 | 4217 | 4374.5 |
| Original transmission module | 6.76% | 6.80% | 6.66% | 6.68% |
| Remove the upper polarizing plate | 413.9 | 418.8 | 381.5 | 396.2 |
| BLU | 4564.5 | 4600.2 | 4210.5 | 4368.5 |
| Remove the transmission of the upper polarizing plate | 9.07% | 9.10% | 9.06% | 9.07% |
| Remove the upper polarizing plate and the lower polarizing plate | 928.7 | 934.2 | 858 | 887.7 |
| BLU | 4559.3 | 4585.7 | 4194.6 | 4360.4 |
| Remove the transmission of the upper polarizing plate and the lower polarizing plate | 20.37% | 20.37% | 20.46% | 20.36% |
| Liquid crystal efficiency | 83.70% | 83.50% | 83% | 82.60% |

TABLE 2

The method of the present disclosure( without considering the dark state )

| | First time | Second time | Third time | Fourth time |
|---|---|---|---|---|
| Remove the upper polarizing plate and attach parallel 255 gray | 76.3 | 75.1 | 72.2 | 72.9 |
| Remove the upper polarizing plate and attach parallel 0 gray | 392.3 | 394.9 | 362.5 | 373.4 |
| Liquid crystal efficiency | 80.50% | 81% | 80.10% | 80.50% |

TABLE 3

The method of the present disclosure ( considering the dark state )

| | First time | Second time | Third time | Fourth time |
|---|---|---|---|---|
| Dark state brightness of the original module | 0.058 | 0.06 | 0.05 | 0.053 |
| Remove the upper polarizing plate and attach parallel 255 gray | 76.3 | 75.1 | 72.2 | 72.9 |
| Remove the upper polarizing plate and attach parallel 0 gray | 392.3 | 394.9 | 362.5 | 373.4 |
| Liquid crystal efficiency | 80.60% | 81% | 80.10% | 80.50% |

According to table 1 to table 3, the liquid crystal efficiencies measured by two methods of the disclosure are close, and, when the contrast of the normally black mode is very high, i.e., the brightness of the dark state is very low, the effect thereof applied to the liquid crystal efficiency can be ignored.

The present disclosure keeps the lower polarizing plate unchanged to make the upper polarizing plate and the lower polarizing of the liquid crystal layer in a first state, in which the polarization axis of the upper polarizing plate is parallel to the polarization axis of the lower polarizing plate; in the first state, the brightness of the screen of the liquid crystal panel is controlled to be 0 gray and the brightness Lvx of the target position of the liquid crystal panel is measured; in the first state, the brightness of the screen of the liquid crystal panel is controlled to be 255 gray and the brightness Lvy of the target position of the liquid crystal panel is measured; according to the brightness Lvx and the brightness Lvy, the liquid crystal efficiency of the liquid crystal layer to the incident light is measured. By the above method, the measurement of the transmittance in the prior art can be avoided; without disassembling the back light module, the effect of the transmittance fluctuation caused by disassembly can be avoid and the measurement can be more accurate and simpler; at the same time, without using the control group, the measured data is measured in the same back light brightness state and the measured data is accurate.

Figure 9:
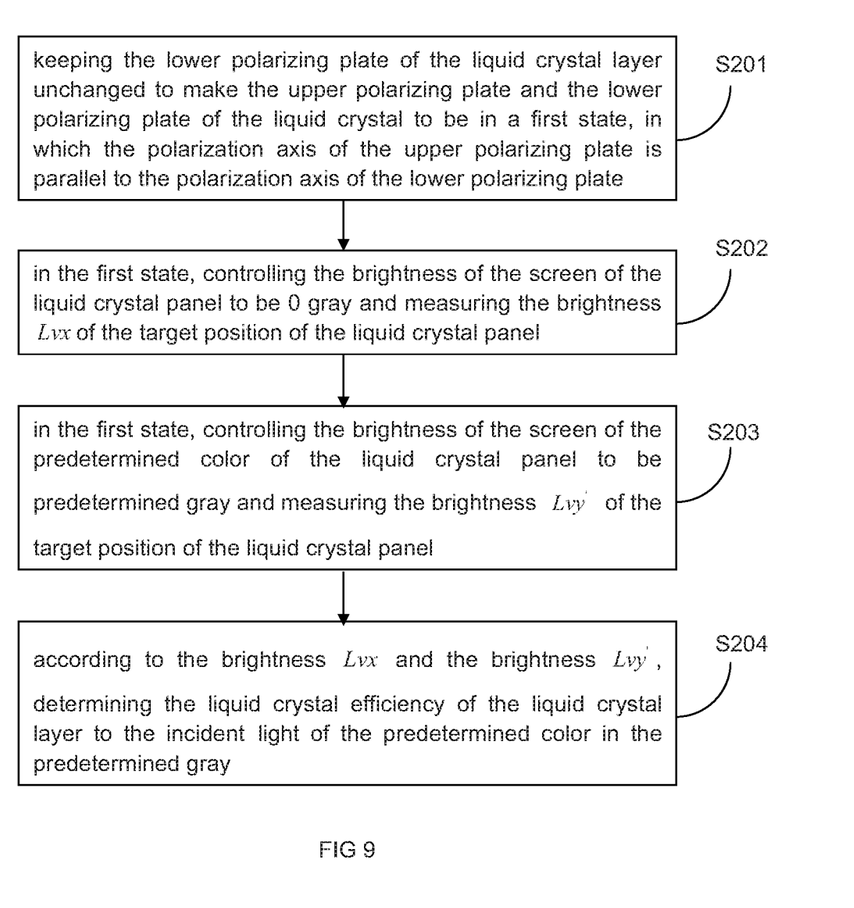
FIG. 9 is a flow chart of an embodiment of the method for measuring the liquid crystal efficiency of the liquid crystal layer to the incident light in the predetermined gray of the present disclosure.

Refer to FIG. 9, FIG. 9 is a flow chart of an embodiment of the method for measuring the liquid crystal efficiency of the liquid crystal layer to the incident light having the predetermined gray according to the present disclosure. The method of the present embodiment is basically the same as the method described above, the part being the same as those in the embodiments can be referred to the detailed description of the above method and are not repeated in detail again; the difference is: first, the 255 gray in the above method is changed to be a predetermined gray, that is, it is possible to measure the brightness Lvy' of the liquid crystal panel in any predetermined gray, and, therefore, the liquid crystal efficiency in the predetermined gray can be measured accordingly; second, the incident light in the above method is changed to be a predetermined color, that is, it is possible to measure the liquid crystal efficiency of any predetermined color in the predetermined gray. The method includes:

Step S201: keeping the lower polarizing plate of the liquid crystal layer unchanged to make the upper polarizing plate and the lower polarizing plate of the liquid crystal to be in a first state, in which the polarization axis of the upper polarizing plate is parallel to the polarization axis of the lower polarizing plate.

Step S202: in the first state, controlling the brightness of the screen of the liquid crystal panel to be 0 gray and measuring the brightness Lvx of the target position of the liquid crystal panel.

Step S203: in the first state, controlling the brightness of the screen of the predetermined color of the liquid crystal panel to be predetermined gray and measuring the brightness Lvy' of the target position of the liquid crystal panel.

Step S204: according to the brightness Lvx and the brightness Lvy', determining the liquid crystal efficiency of the liquid crystal layer to the incident light of the predetermined color in the predetermined gray.

By the above method, it can measure the liquid crystal efficiency of any color and in any gray.

Wherein, the liquid crystal efficiency A' of the liquid crystal layer to the incident light of the predetermined color in the predetermined gray is:

$$A' = \left\{1 - \frac{Lvy'}{Lvx}\right\}\%$$

Wherein, before the step S201, the method may include:

A. making the upper polarizing plate and the lower polarizing of the liquid crystal layer in the second state, in which the polarization axis of the upper polarizing plate is vertical to the polarization axis of the lower polarizing plate.

B. in the second state, controlling the brightness of the screen of the liquid crystal panel to be 0 gray and measuring the brightness Lvz' of the target position of the liquid crystal panel.

At this time, the step S204 specifically is: according to the brightness Lvx, the brightness Lvy' and the brightness Lvz', determining the liquid crystal efficiency of the liquid crystal layer to the incident light of the predetermined color in the predetermined gray.

Wherein, the liquid crystal efficiency B' of the liquid crystal layer to the incident light of the predetermined color in the predetermined gray is:

$$B' = \left\{1 - \frac{Lvy'}{Lvx + Lvz'}\right\}\%$$

Wherein, the step S201 can include: in the second state, removing the original upper polarizing plate, using the new polarizing plate of the same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

Above are only embodiments of the present disclosure and therefore are not to limit the scope of the disclosure, all the equivalent structures or process transformations made by utilizing the contents of the specification and drawings of the present disclosure or applied, either directly or indirectly, to related technologies, are equivalently included in the patent claim scope of the disclosure.

The invention claimed is:

1. A method for measuring a liquid crystal efficiency of a liquid crystal layer to an incident light, wherein, the method comprises:
keeping a lower polarizing plate of the liquid crystal layer unchanged to make an upper polarizing plate and the lower polarizing plate of the liquid crystal layer are in a first state, in which a polarization axis of the upper polarizing plate is parallel to a polarization axis of the lower polarizing plate;
in the first state, controlling a brightness of a screen of a liquid crystal panel to be 0 gray and measuring a brightness Lvx of a target position of the liquid crystal panel;
in the first state, controlling the brightness of the screen of the liquid crystal panel to be 255 gray and measuring a brightness Lvy of the target position of the liquid crystal panel;
according to the brightness Lvx and the brightness Lvy, determining a liquid crystal efficiency A of the liquid crystal layer to the incident light; wherein, the liquid crystal efficiency A of the liquid crystal layer to the incident light is:

$$A = \left\{1 - \frac{Lvy}{Lvx}\right\}\%;$$

or, before the step of keeping the lower polarizing plate of the liquid crystal layer unchanged to make the upper polarizing plate and the lower polarizing plate of the liquid crystal in the first state, the method further comprises:
making the upper polarizer plate and the lower polarizer plate of the liquid crystal layer to be in a second state, in which the polarization axis of the upper polarizing plate is perpendicular to the polarization axis of the lower polarizing plate;
in the second state, controls the brightness of the screen of the liquid crystal panel to be 0 gray and measures a brightness Lvz of the target position of the liquid crystal panel; and
the step of determining the liquid crystal efficiency A of the liquid crystal layer to the incident light according to the brightness Lvx and the brightness Lvy comprising:
determining a liquid crystal efficiency B of the liquid crystal layer to the incident light according to the brightness Lvx, the brightness Lvy and the brightness Lvz.

2. The method according to claim 1, wherein, the liquid crystal efficiency B of the liquid crystal layer to the incident light is:

$$B = \left\{1 - \frac{Lvy}{Lvx + Lvz}\right\}\%.$$

3. The method according to claim 1, wherein, the step of keeping the lower polarizing plate of the liquid crystal layer unchanged to make the upper polarizing plate and the lower polarizing plate of the liquid crystal in the first state, comprises:
in the second state, removing an original upper polarizing plate, using a new polarizing plate of a same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

4. A method for measuring a liquid crystal efficiency of a liquid crystal layer to an incident light, wherein, the method comprises:
keeping a lower polarizing plate of the liquid crystal layer unchanged to make an upper polarizing plate and the lower polarizing plate of the liquid crystal layer are in a first state, in which a polarization axis of the upper polarizing plate is parallel to a polarization axis of the lower polarizing plate;
in the first state, controlling a brightness of a screen of a liquid crystal panel to be 0 gray and measuring a brightness Lvx of a target position of the liquid crystal panel;
in the first state, controlling the brightness of the screen of the liquid crystal panel to be 255 gray and measuring a brightness Lvy of the target position of the liquid crystal panel;
according to the brightness Lvx and the brightness Lvy, determining a liquid crystal efficiency A of the liquid crystal layer to the incident light.

5. The method according to claim 4, wherein, the liquid crystal efficiency A of the liquid crystal layer to the incident light is:

$$A = \left\{1 - \frac{Lvy}{Lvx}\right\}\%.$$

6. The method according to claim 4, wherein, before the step of keeping the lower polarizing plate of the liquid crystal layer unchanged to make the upper polarizing plate and the lower polarizing plate of the liquid crystal in the first state, comprises:

making the upper polarizer plate and the lower polarizer plate of the liquid crystal layer to be in a second state, in which the polarization axis of the upper polarizing plate is perpendicular to the polarization axis of the lower polarizing plate;

in the second state, controlling the brightness of the screen of the liquid crystal panel to be 0 gray and measuring a brightness Lvz of the target position of the liquid crystal panel;

the step of determining the liquid crystal efficiency A of the liquid crystal layer to the incident light according to the brightness Lvx and the brightness Lvy comprising:

determining a liquid crystal efficiency B of the liquid crystal layer to the incident light according to the brightness Lvx, the brightness Lvy and the brightness Lvz.

7. The method according to claim 6, wherein, the liquid crystal efficiency B of the liquid crystal layer to the incident light is:

$$B = \left\{1 - \frac{Lvy}{Lvx + Lvz}\right\}\%.$$

8. The method according to claim 6, wherein, the step of keeping the lower polarizing plate of the liquid crystal layer unchanged to make the upper polarizing plate and the lower polarizing plate of the liquid crystal in the first state, comprises:

in the second state, removing an original upper polarizing plate, using a new polarizing plate of a same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

9. A method for measuring a liquid crystal efficiency of a liquid crystal layer to an incident light in a predetermined gray, wherein, the method comprises:

keeping a lower polarizing plate of the liquid crystal layer unchanged to make an upper polarizing plate and the lower polarizing plate of the liquid crystal layer are in a first state, in which a polarization axis of the upper polarizing plate is parallel to a polarization axis of the lower polarizing plate;

in the first state, controlling a brightness of a screen of a liquid crystal panel to be 0 gray and measuring a brightness Lvx of a target position of the liquid crystal panel;

in the first state, controlling the brightness of the screen of a predetermined color of the liquid crystal panel to be a predetermined gray and measuring a brightness Lvy' of the target position of the liquid crystal panel;

according to the brightness Lvx and the brightness Lvy', determining a liquid crystal efficiency A' of the liquid crystal layer to the incident light of the predetermined color in the predetermined gray.

10. The method according to claim 9, wherein, the liquid crystal efficiency A' of the liquid crystal layer to the incident light of the predetermined color in the predetermined gray is:

$$A' = \left\{1 - \frac{Lvy'}{Lvx}\right\}\%.$$

11. The method according to claim 9, wherein, before the step of keeping the lower polarizing plate of the liquid crystal layer unchanged to make the upper polarizing plate and the lower polarizing plate of the liquid crystal in the first state, comprises:

making the upper polarizer plate and the lower polarizer plate of the liquid crystal layer to be in a second state, in which the polarization axis of the upper polarizing plate is perpendicular to the polarization axis of the lower polarizing plate;

in the second state, controlling the brightness of the screen of the liquid crystal panel to be 0 gray and measuring a brightness Lvz' of the target position of the liquid crystal panel;

the step of determining the liquid crystal efficiency A' of the liquid crystal layer to the incident light according to the brightness Lvx and the brightness Lvy' comprising:

determining a liquid crystal efficiency B' of the liquid crystal layer to the incident light of the predetermined color in the predetermined gray according to the brightness Lvx, the brightness Lvy' and the brightness Lvz'.

12. The method according to claim 11, wherein, the liquid crystal efficiency B' of the liquid crystal layer to the incident light of the predetermined color in the predetermined gray is:

$$B' = \left\{1 - \frac{Lvy'}{Lvx + Lvz'}\right\}\%.$$

13. The method according to claim 11, wherein, the step of keeping the lower polarizing plate of the liquid crystal layer unchanged to make the upper polarizing plate and the lower polarizing plate of the liquid crystal in the first state, comprises:

in the second state, removing an original upper polarizing plate, using a new polarizing plate of a same model of the original upper polarizing plate as the upper polarizing plate and attaching the new polarizing plate by deflecting 90 degrees from a polarizer attach direction along which the original upper polarizing plate being attached so as to make the upper polarizing plate and the lower polarizing plate of the liquid crystal layer to be in the first state.

* * * * *